US010930134B2

United States Patent
Zhang et al.

(10) Patent No.: US 10,930,134 B2
(45) Date of Patent: Feb. 23, 2021

(54) HAND HYGIENE MONITORING SYSTEM AND ITS APPLICATION METHOD

(71) Applicant: Hangzhou Smalliot Technology Co., Ltd., Hangzhou (CN)

(72) Inventors: Fengxiang Zhang, Hangzhou (CN); Yimin Wu, Hangzhou (CN); Weixiang Zhang, Hangzhou (CN); Zhibo Li, Hangzhou (CN)

(73) Assignee: HANGZHOU SMALLIOT TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 16/655,274

(22) Filed: Oct. 17, 2019

(65) Prior Publication Data
US 2020/0380849 A1 Dec. 3, 2020

(30) Foreign Application Priority Data
May 31, 2019 (CN) .......................... 201910468811.7

(51) Int. Cl.
*G08B 1/08* (2006.01)
*G08B 21/24* (2006.01)
*G16H 40/67* (2018.01)
*G16H 40/20* (2018.01)
*G08B 7/06* (2006.01)

(52) U.S. Cl.
CPC ............. *G08B 21/245* (2013.01); *G08B 7/06* (2013.01); *G16H 40/20* (2018.01); *G16H 40/67* (2018.01)

(58) Field of Classification Search
CPC ........ G08B 21/245; G08B 7/06; G16H 40/67; G16H 40/20

USPC ...................................................... 340/539.13
See application file for complete search history.

(56) References Cited

U.S. PATENT DOCUMENTS

| | | | | |
|---|---|---|---|---|
| 8,395,515 B2* | 3/2013 | Tokhtuev | ............... | G06Q 10/00 340/603 |
| 9,483,930 B1* | 11/2016 | Haaland | .................. | A61B 90/80 |
| 10,403,121 B2* | 9/2019 | Liu | ..................... | G06K 7/10366 |
| 10,679,488 B2* | 6/2020 | Liu | ......................... | G16H 50/30 |
| 2010/0117823 A1* | 5/2010 | Wholtjen | ............. | G08B 21/245 340/539.13 |
| 2015/0035678 A1* | 2/2015 | Long | .................... | G08B 21/245 340/573.1 |
| 2015/0161874 A1* | 6/2015 | Thyroff | .................. | G08B 25/10 340/539.11 |
| 2016/0140831 A1* | 5/2016 | Hermann | ............... | G08B 21/24 340/573.1 |

(Continued)

FOREIGN PATENT DOCUMENTS

| | | |
|---|---|---|
| CN | 105139320 A | 12/2015 |
| CN | 206133696 U | 4/2017 |

*Primary Examiner* — Zhen Y Wu
(74) *Attorney, Agent, or Firm* — Sayramoglu Law Offices LLC

(57) ABSTRACT

A hand hygiene monitoring system includes an identity authentication module, a motion acquisition module and a judgment module; where the identity authentication module is for identifying the person being detected; the motion acquisition module includes a sensor device; the judgment module includes a processing chip, which makes calibrated data available for a motion algorithm; the motion algorithm includes movement direction algorithm and motion trajectory algorithm.

7 Claims, 2 Drawing Sheets

(56) References Cited

U.S. PATENT DOCUMENTS

| | | | | |
|---|---|---|---|---|
| 2017/0220131 A1* | 8/2017 | Huang | ............... | G06K 9/00355 |
| 2018/0293873 A1* | 10/2018 | Liu | ................... | G06K 7/10366 |
| 2018/0357886 A1* | 12/2018 | Tavori | .................... | G06F 1/163 |
| 2019/0043337 A1* | 2/2019 | Liu | ........................ | G16H 40/20 |
| 2019/0197873 A1* | 6/2019 | Hermann | ............. | G08B 21/245 |
| 2019/0228640 A1* | 7/2019 | Freedman | ............... | G16H 40/20 |
| 2020/0074835 A1* | 3/2020 | Waghode | ............... | G16H 40/63 |

* cited by examiner

HAND HYGIENE MONITORING SYSTEM AND ITS APPLICATION METHOD

CROSS REFERENCE TO THE RELATED APPLICATIONS

This application is based upon and claims priority to Chinese Patent Application No. 201910468811.7, filed on May 31, 2019, the entire contents of which are incorporated herein by reference.

TECHNICAL FIELD

The present disclosure relates to the field of healthcare associated behavioral monitoring technology, and discloses a hand hygiene monitoring system and its application method.

BACKGROUND

Hand-borne bacteria are the main source of nosocomial infections among medical staff. More than 30% of hospital infections are nosocomial infections caused by hand-borne bacteria directly or indirectly. Strict hand washing by medical staff can reduce the carrying of pathogens and effectively cut off direct contact transmission.

The Hand Hygiene Guide for medical institutions issued in October 2002 by CDC, the Centers for Disease Control and Prevention, an United States federal agency, confirms the effectiveness of hand hygiene, and it points out that hand hygiene is one of the most direct, simple, economical and effective measures to reduce nosocomial infection compared with other nosocomial infection management measures. It plays an imperative role in nosocomial infection in hospitals and can reduce the incidence of nosocomial infection by 50%.

The low compliance rate of hand hygiene is long a common problem in all level hospitals in China and other countries alike. How to effectively improve the compliance rate of hand hygiene in hospitals becomes a major concern for hospital infection control leaders. At present, hospitals mainly rely on traditional management methods such as regular training, self-restraint of medical staff, setting up infection commissioner, etc. They still lack effective measures for hand hygiene supervision, resultantly wasting a lot of manpower and material resources, and greatly increasing the hidden cost of hospitals.

On the other hand, there are also some technologies or products aimed at improving the compliance rate of hand hygiene in hospitals. For example, China's patent "An Intelligent Supervision System for Medical Hand Hygiene Compliance" (CN 105139320A) and "An Intelligent Supervision System for Medical Behavior Management" (CN206133696U) have both disclosed specific monitoring systems. Their systems establish wireless communication between terminals and monitoring platform by 433 M/2.4 G and 125K radio frequency signal, collect the activity routes and contact ranges of medical workers through terminals, and monitor hand hygiene situations through monitoring platform.

However, these similar monitoring systems have the following shortcomings:

They only use the low frequency 125K radio frequency signal to sense the distance, which can only solve the problem of identification but not the judgment of whether the source of infection has really been contacted. Its judgment method is like this, once the low frequency 125K signal is detected near the bedside, it concludes that the source of infection has been contacted. This is often not the case in the real clinical scenes, most likely it will be misjudged as being in direct contact with the source of infection.

For scenarios prior to contacting patients, it is impossible to judge whether a medical worker has contacted patients only by sensing distance, thus leads to misjudgment of hand hygiene opportunities before contacting patients, and causes extra burden to medical workers.

For scenarios prior to cleaning or aseptic operation, it is impossible to distinguish whether a medical worker is performing aseptic operation only by sensing distance. When a medical worker enters the monitoring area, it concludes that the medical work performs aseptic operation, thus is inaccurate, resultantly often leading to misjudgments and causing unnecessary burden to medical workers.

SUMMARY

In view of the disadvantages of inaccurate judgment, large workload and low efficiency in the prior art, the present disclosure provides a hand hygiene monitoring system and its application method.

The present disclosure solves above mentioned technical problems by the following solutions.

A hand hygiene monitoring system consists of an identity authentication module, a motion acquisition module and a judgment module.

The identity authentication module is used to identify the identity the person being detected, and the motion acquisition module is activated after the identity is successfully recognized.

The motion acquisition module includes a sensor device, which is placed on the badge of the person being detected to obtain the motion data generated by the person when washing hands or doing other actions, and transmit the static error calibration of the motion data to the judgment module.

The judgment module includes a processing chip, which feeds the calibrated data into the motion algorithm. The motion algorithm includes the movement direction algorithm and movement trajectory algorithm. It is used to judge whether the motion is a trigger action or not, and finally to judge whether the hand washing is completed according to the trigger action.

As a preferred embodiment, the identity authentication module includes a transmitter and an identification device, wherein the transmitter is installed in a fixed position of the ward and transmits signals, and the identification device, which is worn by a medical worker as a badge and usually put in sleep mode, receives signals within a range and deciphers information, when receiving the signal of the transmitter the identification device will awake and perform authentication, it proceeds to the next phase after a successful authentication.

As a preferred embodiment, the sensor is a six-axis motion signal processing module, which includes gyroscope sensor and gravitational acceleration sensor. The gyroscope sensor is used to detect the angular velocity of the subject while the gravitational acceleration sensor is used to monitor the gravitational acceleration of the subject. The angular velocity and gravitational acceleration are both motion related data.

As a preferred embodiment, the static error calibration process of motion data consists of feeding the angular velocity data and gravitational acceleration data through Kalman filter to eliminate random noise.

As a preferred embodiment, the movement direction algorithm includes the following steps:
(1) Set the right-handed reference coordinate system;
(2) Read the angular velocity data from the gyroscope sensor and the gravitational acceleration data from the gravitational acceleration sensor;
(3) Put the data collected in step (2) into DMP database for data processing and conversion into quaternion;
(4) Send the angular velocity, gravitational acceleration and the converted quaternion data to the buffer queue through the interface at a frequency of 200 Hz;
(5) Processing chip reads data from the buffer queue at a frequency of 300 Hz, then converts quaternion data into Euler angle by the quaternion algorithm. The Euler angle includes pitch angle P, roll angle R and yaw angle Y. The calculation algorithms are as follows: suppose quaternion is (q0, q1, q2 and q3), respectively;

$$P = a \sin(-2*q1*q3 + 2*q0*q2)*57.3;$$

$$R = a \tan2(2*q2*q3 + 2*q0*q1, -2*q1*q1 - 2*q2*q2 + 1)*57.3;$$

$$Y = a \tan2(2*(q1*q2 + q0*q3), q0*q0 + q1*q1 - q2*q2 - q3*q3)*57.3.$$

As a preferred embodiment, the trajectory algorithm follows as below, let n be the signal scanning period, s(n) be the motion displacement function, the motion coordinate system be [x, y, z], a(n) be the angular velocity, and g(n) be the gravitational acceleration, put them in the equation, let the initial position $s(t^0)=0$, $$[s_{x_n}, s_{y_n}, s_{z_n}] = \left[ s_{x_{n-1}} + V_{x_{n-1}} \Delta t + \frac{1}{4}(a_{x_{n-1}} + a_{x_n})\Delta t^2, \right.$$
$$\left. s_{y_{n-1}} + V_{y_{n-1}} \Delta t + \frac{1}{4}(a_{y_{n-1}} + a_{y_n})\Delta t^2, s_{z_{n-1}} + V_{z_{n-1}} \Delta t + \frac{1}{4}(a_{z_{n-1}} + a_{z_{n-1}})\Delta t^2 \right]$$

Here, n>1, Δt is the time interval value.

As a preferred embodiment, after the trigger action is detected by the processing chip, the current hand hygiene status will be changed into the state of clean-required; after the hand washing action is detected by the processing chip, the current hand hygiene status will be changed into the clean state.

As a preferred embodiment, the hand hygiene monitoring system further includes an alarm module, the alarm module is an acousto-optic alarm device, and the acousto-optic alarm device connected with a processing chip is used to prompt the examinee to judge the result.

A hand hygiene monitoring system and its application method consists of the following steps:
(1) Identity recognition: When a person enters the recognition area and is identified, the motion acquisition module is activated to acquire the motion data of the person.
(2) Hand washing detection: After entering the cleaning area, the person is subject to the hand washing detection by default. The six-axis motion processing chip of the motion acquisition module placed in the badge of the person acquires the movement direction data and trajectory data, the processing chip judges whether the movement of the person is a cleaning action, if it is a cleaning action, the current state will be changed to a clean state; otherwise it sends a message to the alarm module for warning;
(3) Motion Acquisition: After entering the operation area, during the operation of the medical worker, the movement direction data and trajectory data of the person are acquired by the six-axis motion processing module placed in the badge of the person and sent to the processing chip until the person leaves the operation area.
(4) Action judgment: By the movement direction data and trajectory data acquired in step (3), the processing chip judges whether the current motion action of the person is the trigger action or not. If it is the trigger action, the processing chip changes the current state as clean-required; otherwise it sets the state as clean.
(5) Judgment after completion of the operation: After the medical worker completes operation and enters the cleaning area, if the current state is clean required, repeat step (2); if the current state is a clean state, the person can exit the cleaning area directly.

As a preferred embodiment, from step (2) to step (5), the judgment process consists of judgment interval period, which is 10~15 seconds.

Due to the adopting of the above technical scheme, the present disclosure has remarkable application effects: in medical associated environment, the overall hand hygiene compliance of the hospital departments equipped with the system has been significantly improved, with the effectiveness being stable, resulting great reduction of the incidence of nosocomial infection and the average hospitalization days of patients; while combining with identity authentication module and motion acquisition module, the present disclosure can more accurately judge the movement trajectory and actions of medical workers in the room, so as to avoid misjudgment and improve the accuracy of hand hygiene compliance rate as well as user experience.

BRIEF DESCRIPTIONS OF THE DRAWINGS

DETAILED DESCRIPTION OF THE EMBODIMENTS

The present disclosure is described below in further details in connection with the drawings and examples.

In Embodiment 1

Figure 1:
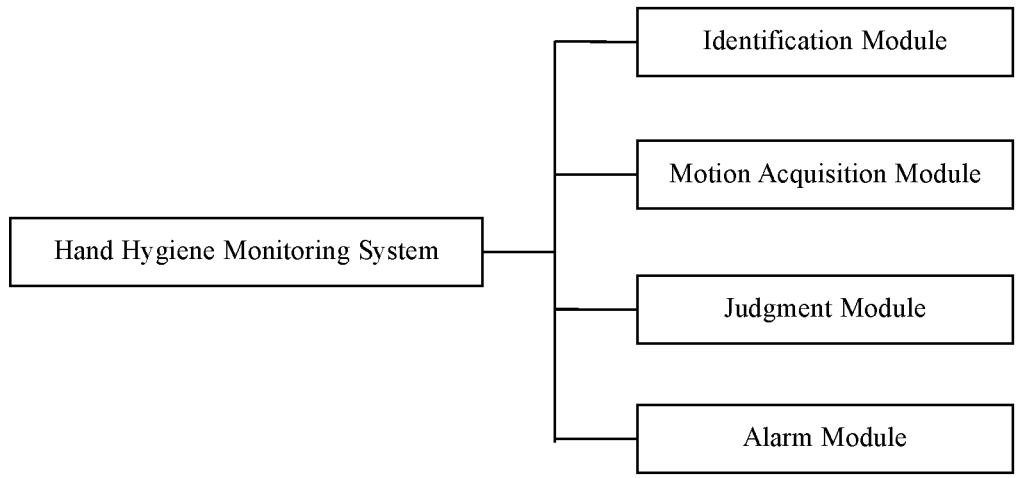
FIG. 1 is the schematic illustration of the structure of the present disclosure, a hand hygiene monitoring system and its application method.
Figure 2:
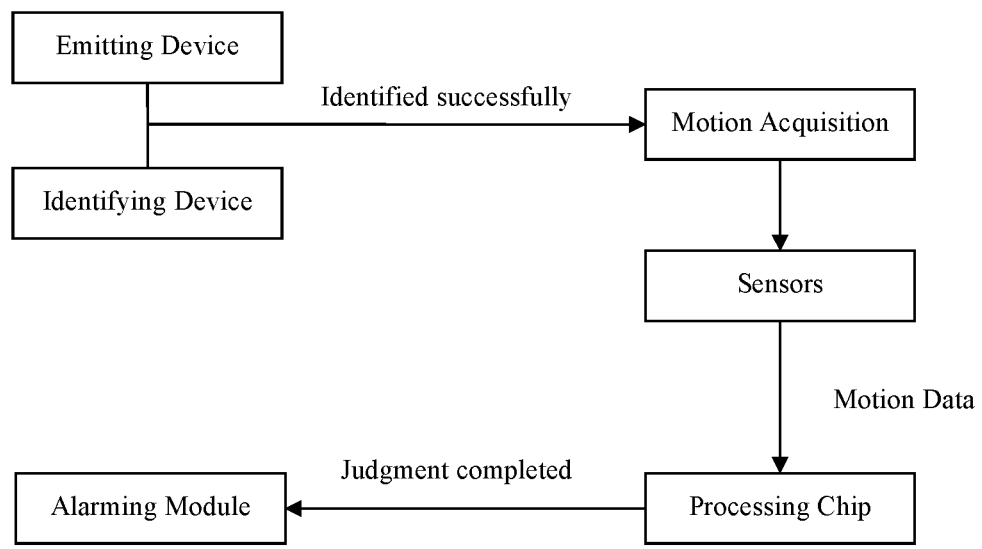
FIG. 2 is the schematic illustration of the scheme of the present disclosure, a hand hygiene monitoring system and its application method.
Figure 3:
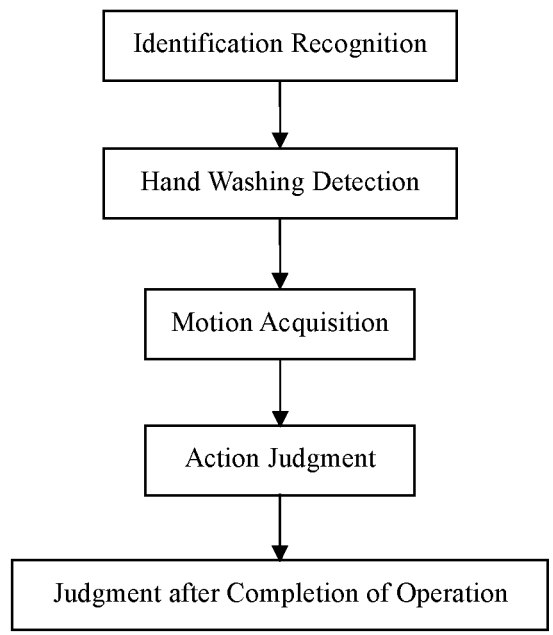
FIG. 3 is the schematic illustration of the workflow of the present disclosure, a hand hygiene monitoring system and its application method.

As illustrated from FIG. 1 to FIG. 3, a hand hygiene monitoring system is characterized by: an identity authentication module, a motion acquisition module and a judgment module;

The identity authentication module is used to identify the person being detected, and the motion acquisition module is activated after the identity is successfully recognized.

The motion acquisition module includes a sensor device, which is placed on the badge of the person being detected to obtain the motion data generated by the person when washing hands or doing other actions, and transmit the static error calibration of the motion data to the judgment module.

The judgment module includes a processing chip, which feeds the calibrated data into the motion algorithm. The motion algorithm includes the movement direction algorithm and movement trajectory algorithm. It is used to judge whether the motion is a trigger action or not, and finally to judge whether the hand washing is completed according to the trigger action.

The identity authentication module includes a transmitter and an identification device, wherein the transmitter is installed in a fixed position of the ward and transmits signals, and the identification device, which is worn by a medical worker as a badge and usually put in sleep mode, receives signals within a range and deciphers information, when receiving the signal of the transmitter the identification device will awake and perform authentication, it proceeds to the next phase after a successful authentication.

The sensor is a six-axis motion signal processing module, which includes gyroscope sensor and gravitational acceleration sensor. The gyroscope sensor is used to detect the angular velocity of the subject while the gravitational acceleration sensor is used to monitor the gravitational acceleration of the subject. The angular velocity and gravitational acceleration are both motion related data.

The static error calibration process of motion data consists of feeding the angular velocity data and gravitational acceleration data through Kalman filter to eliminate random noise.

The movement direction algorithm includes the following steps:
(1) Set the right-handed reference coordinate system;
(2) Read the angular velocity data from the gyroscope sensor and the gravitational acceleration data from the gravitational acceleration sensor;
(3) Put the data collected in step (2) into DMP database for data processing and conversion into quaternion;
(4) Send the angular velocity, gravitational acceleration and the converted quaternion data to the buffer queue through the interface at a frequency of 200 Hz;
(5) Processing chip reads data from the buffer queue at a frequency of 300 Hz, then converts quaternion data into Euler angle by the quaternion algorithm. The Euler angle includes pitch angle P, roll angle R and yaw angle Y. The calculation algorithms are as follows: suppose quaternion is (q0, q1, q2 and q3), respectively;

$$P = a\sin(-2*q1*q3 + 2*q0*q2)*57.3;$$

$$R = a\tan2(2*q2*q3 + 2*q0*q1, -2*q1*q1 - 2*q2*q2 + 1)*57.3;$$

$$Y = a\tan2(2*(q1*q2 + q0*q3), q0*q0 + q1*q1 - q2*q2 - q3*q3)*57.3.$$

The trajectory algorithm follows as below, let n be the signal scanning period, s(n) be the motion displacement function, the motion coordinate system be [x, y, z], a(n) be the angular velocity, and g(n) be the gravitational acceleration, put them in the equation, let the initial position $s(t^0)=0$, $$[s_{x_n}, s_{y_n}, s_{z_n}] = \left[s_{x_{n-1}} + V_{x_{n-1}}\Delta t + \frac{1}{4}(a_{x_{n-1}} + a_{x_n})\Delta t^2,\right.$$
$$\left. s_{y_{n-1}} + V_{y_{n-1}}\Delta t + \frac{1}{4}(a_{y_{n-1}} + a_{y_n})\Delta t^2, s_{z_{n-1}} + V_{z_{n-1}}\Delta t + \frac{1}{4}(a_{z_{n-1}} + a_{z_n})\Delta t^2\right]$$

here, n>1, $\Delta t$ is the time interval value.

After the trigger action is detected by the processing chip, the current hand hygiene status will be changed into the state of clean-required; after the hand washing action is detected by the processing chip, the current hand hygiene status will be changed into the clean state.

It consists of an alarm module, the alarm module is an acousto-optic alarm device, and the acousto-optic alarm device connected with a processing chip is used to prompt the examinee to judge the result.

A hand hygiene monitoring system and its application method consists of the following steps:
(1) Identity recognition: When a person enters the recognition area and is identified, the motion acquisition module is activated to acquire the motion data of the person.
(2) Hand washing detection: After entering the cleaning area, the person is subject to the hand washing detection by default. The six-axis motion processing chip of the motion acquisition module placed in the badge of the person acquires the movement direction data and trajectory data, the processing chip judges whether the movement of the person is a cleaning action, if it is a cleaning action, the current state will be changed to a clean state; otherwise it sends a message to the alarm module for warning;
(3) Motion Acquisition: After entering the operation area, during the operation of the medical worker, the movement direction data and trajectory data of the person are acquired by the six-axis motion processing module placed in the badge of the person and sent to the processing chip until the person leaves the operation area.
(4) Action judgment: By the movement direction data and trajectory data acquired in step (3), the processing chip judges whether the current motion action of the person is the trigger action or not. If it is the trigger action, the processing chip changes the current state as clean-required; otherwise it sets the state as clean.
(5) Judgment after completion of the operation: After the medical worker completes operation and enters the cleaning area, if the current state is clean required, repeat step (2); if the current state is a clean state, the person can exit the cleaning area directly.

From step (2) to step (5), the judgment process consists of judgment interval period, which is 10~15 seconds.

In medical associated environment, the overall hand hygiene compliance of the hospital departments equipped with the system has been significantly improved, with the effectiveness being stable, resulting great reduction of the incidence of nosocomial infection and the average hospitalization days of patients; while combining with identity authentication module and motion acquisition module, the hand hygiene monitoring system can more accurately judge the movement trajectory and actions of medical workers in the room, so as to avoid misjudgment and improve the accuracy of hand hygiene compliance rate as well as user experience.

In Embodiment 2

In the present embodiment, the part model of the six-axis motion processing module is MPU6500, which is placed in the badge of medical workers.

When a medical worker wearing the badge enters the ward, the badge will activate the gyroscope sensor and acceleration sensor for data acquisition. The angular velocity and acceleration data collected from X, Y and Z axes will be processed and converted into quaternion data through the DMP Library of MPU6500. Then the acceleration, angular velocity and quaternion data are sent to the buffer queue at the frequency of 200 Hz via the I2C interface; on the other hand, the processing chip MSP430 reads the data from the buffer queue at the frequency of 300 Hz; afterwards, the angular velocity and acceleration data are fed through Kalman filter to eliminate random noise, and the motion trajectory is obtained by integral operation of the filtered acceleration data. The quaternion algorithm converts the quaternion data into Euler angle (Pitch, Roll and Yaw), combining them together to realize the motion trajectory judgment function of the medical worker. The specific steps are as follows:

Step 1, set the right-hand reference coordinate system (OXgYgZg), where the reference coordinate system is the default coordinate system of MPU6500;

Step 2, the gyroscope sensor performs data acquisition (ax, ay, az), the gravitational acceleration sensor performs data acquisition (gx, gy, gz);

Step 3, MPU6500 puts the data collected in the first step into its own DMP library for data processing and conversion into quaternions (q0, q1, q2, q3);

Step 4: MPU6500 sends the angular velocity (ax, ay, az), the gravitational acceleration (gx, gy, gz) and converted quaternion (q0, q1, q2, q3) data to the buffer queue through the I2C interface at the frequency of 200 Hz. The larger the buffer queue, the smoother the final parsed action will be;

Step 5: MSP430 reads data from the buffer queue at the frequency of 300 Hz, and then calculates the movement direction and trajectory using the corresponding algorithms. The two algorithms are as follows:

1 The quaternion algorithm converts the quaternion data into Euler angle (Pitch, Roll and Yaw) as below, $$P = a\sin(-2*q1*q3 + 2*q0*q2)*57.3;$$

$$R = a\tan2(2*q2*q3 + 2*q0*q1, -2*q1*q1 - 2*q2*q2 + 1)*57.3;$$

$$Y = a\tan2(2*(q1*q2 + q0*q3), q0*q0 + q1*q1 - q2*q2 - q3*q3)*57.3.$$

2 The motion trajectory is calculated using integral operation as below, Set the initial condition $s(t^0) = 0$, $$s(t) = \int_{t0}^{t} v(t)dt = \frac{v_{(t_0)} + v_{(t_1)}}{2}(t_1 - t_0) + \frac{v_{(t_1)} + v_{(t_2)}}{2}(t_2 - t_1) + \ldots + \frac{v_{(t_{n-1})} + v_{(t_n)}}{2}(t_n - t_{n-1}) \quad (1)$$

Set $\Delta t = t_1 - t_0 = t_2 - t_1 = \ldots = t_n - t_{n-1}$, $\Delta t$ is time interval, in the scattered domain, when n>1, $$v(n) = \sum_{k=0}^{n} \frac{a(k-1) + a(k)}{2} \Delta t = \quad (2)$$

$$\frac{1}{2}[a(0) + a(n)]\Delta t + [a(1) + a(2) + \ldots + a(n-1)]\Delta t + v(0)$$

$$s(n) = \sum_{k=0}^{n} \frac{v(k+1) + v(k)}{2} \Delta t = \quad (3)$$

$$\frac{1}{2}[v(0) + v(n)]\Delta t + [v(1) + v(2) + \ldots + v(n-1)]\Delta t$$

Derived from (2) and (3), $$v(n) = v(n-1) + \frac{a(n) + a_{(n-1)}}{2} \cdot \Delta t \quad (4)$$

$$s(n) = s(n-1) + \frac{v(n) + v(n-1)}{2} \cdot \Delta t = \quad (5)$$

$$s(n-1) + v(n-1) \cdot \Delta t + \frac{1}{4}[a(n-1) + a(n)] \cdot \Delta t^2$$

From (4) and (5), the instantaneous velocity v(n) and motion displacement s(n) can be calculated from s(n−1), v(n−1), a(n−1), and current a(n). By applying the deduced results v(n), s(n) of (4) and (5) to the acceleration sensor, the three-dimensional spatial displacement formula can be obtained as follows:

$$[x_0, y_0, z_0] = [s_{x_0}, s_{y_0}, s_{z_0}] \quad (6)$$

$$[x_0, y_0, z_0] = [s_{x_1}, s_{y_1}, s_{z_1}] = \quad (7)$$
$$[s_{x_0}, s_{y_1}, s_{z_1}] = \left[ s_{x_0} + V_{x_0}\Delta t + \frac{1}{4}(a_{x_0 + a_{x_1}})\Delta t^2, \right.$$
$$\left. s_{y_0} + V_{y_0}\Delta t + \frac{1}{4}(a_{y_0 + a_{y_1}})\Delta t^2, s_{z_0} + V_{z_0}\Delta t + \frac{1}{4}(a_{z_0 + a_{z_1}})\Delta t^2 \right]$$

...

$$[x_n, y_n, z_n] = [s_{x_n}, s_{y_n}, s_{z_n}] = \left[ s_{x_{n-1}} + V_{x_{n-1}}\Delta t + \frac{1}{4}(a_{x_{n-1} + a_{x_n}})\Delta t^2, \right. \quad (8)$$
$$s_{y_{n-1}} + V_{y_{n-1}}\Delta t + \frac{1}{4}(a_{y_{n-1} + a_{y_n}})\Delta t^2,$$
$$\left. s_{z_{n-1}} + V_{z_{n-1}}\Delta t + \frac{1}{4}(a_{z_{n-1} + a_{z_{n-1}}})\Delta t^2 \right]$$

According to the integral method, the calculation of a motion trajectory requires 2*3*n times of integral operation. By using Newton's motion theorem and trapezoidal method in calculus, the whole operation can be simplified to 2*3*n times of addition calculation, which greatly improves the calculation efficiency.

The pitch angle Pitch, its value will undergo changes to some extent before and after the bending actions of a medical worker. With these series of values, the bending trajectory of the medical worker can be calculated. When the obtained pitch angle Pitch gives a movement trajectory from 90 degrees to 60 degrees, it will be judged that the medical worker has bent down. On this basis, the medical worker can be judged whether or not to bend down to operate on patients at the bedside, so as to distinguish between conducting ward rounds and operating on patients, as a result, to actuate different sound and light reminders. Only when a medical worker really bends down to operate patients at the bedside will hand hygiene reminder be carried out, thus improving the reliability and authenticity of compliance rate.

When a medical worker washes his or her hands by WHO's standard seven-step washing method, Pitch, Roll and Yaw changes values to form a certain hand washing movement trajectory. After some model training, the empirical value intervals can be obtained. When the hand washing movement trajectory of the medical worker is within the empirical value intervals, it will be judged as successful hand washing and the event will be recorded while the badge changes to the clean state. In this case, hand hygiene reminders will not fire when the medical worker performs other operations.

In Embodiment 3

Embodiment 3 is similar to Embodiment 2, except for the following,

When a medical worker reaches out to hang the liquid bottle, the coordinates of the badge worn by the medical worker will change to a certain extent, forming a short-distance trajectory, while the pitch angle will also form a certain angle trajectory. By the comprehensive judgement of the two trajectories, the judgement of hanging the liquid bottle can be realized. After identifying that the medical worker reaches out to hang the liquid bottle, the badge's state will change from the clean state to the state of clean required. Hand hygiene reminder will fire when they perform other operations afterward.

When a medical worker's body sways due to operating injection or shaking liquid bottles, the Z-axis of body coordinates will change accordingly. When values on the other two axes change below certain thresholds while the values on the Z-axis change over certain thresholds, it will be judged that the medical worker sways due to operation on patients, and the badge's state will change from the clean state to the state of clean required. Hand hygiene reminder will fire when the medical worker performs other operations afterward.

In conclusion, the above mentioned are only some preferred specific embodiments of the present disclosure, various changes and modifications can be made to the disclosure within the scope and range of equivalents of the claims and without departing from the disclosure.

What is claimed is:

1. A hand hygiene monitoring system comprising:
an identity authentication module, a motion acquisition module and a judgment module;
the identity authentication module is configured to identify a person being detected, and a motion acquisition module is activated after an identity of the person is successfully recognized;
the motion acquisition module includes a sensor device, the sensor device is placed on a badge of the person being detected to obtain a motion data generated by the person when washing hands, and transmit a static error calibration of the motion data to the judgment module;
the judgment module includes a processing chip, the processing chip feeds the calibrated data into a motion algorithm; the motion algorithm includes a movement direction and movement trajectory algorithm; wherein the movement direction and movement trajectory algorithm judges whether a motion is a trigger action or not, and whether a hand washing is completed according to the trigger action;
wherein the sensor device is a six-axis motion signal processing module including a gyroscope sensor and a gravitational acceleration sensor; the gyroscope sensor is configured to detect an angular velocity of the person while the gravitational acceleration sensor is configured to monitor a gravitational acceleration of the person;

wherein the angular velocity and the gravitational acceleration are both motion related data;
wherein the static error calibration of the motion data consists of feeding the angular velocity data and the gravitational acceleration data through a Kalman filter to eliminate random noise;
wherein the movement direction algorithm is configured to perform following steps:
(1) set a right-handed reference coordinate system;
(2) read the angular velocity data from the gyroscope sensor and the gravitational acceleration data from the gravitational acceleration sensor;
(3) put the angular velocity data and the gravitational acceleration data into a Data Management Platform database for data processing and conversion into a quaternion data;
(4) send the angular velocity, the gravitational acceleration and the quaternion data to a buffer queue through an interface at a frequency of 200 Heinrich Hertz;
wherein the processing chip reads data from the buffer queue at a frequency of 300 Hz, then converts the quaternion data into a Euler angle by a quaternion algorithm;
the Euler angle includes a pitch angle P, a roll angle R and a yaw angle Y;
wherein P=asin (−2*q1*q3+2*q0*q2)*57.3;
R=atan2 (2*q2*q3+2*q0*q1, −2*q1*q1−2*q2*q2+1)*57.3;
Y=atan2 (2*(q1*q2+q0*q3), q0*q0+q1*q1−q2*q2−q3*q3)*57.3;
wherein the quaternion data is (q0, q1, q2 and q3), respectively.

2. The hand hygiene monitoring system according to claim 1, wherein the identity authentication module includes a transmitter and an identification device, wherein the transmitter is installed in a fixed position of a ward and transmits signals, and the identification device is worn by the person as the badge and signals within a range and deciphers information, when receiving the signal of the transmitter the identification device will awakes from a sleep mode and performs authentication, and proceeds to a next phase after a successful authentication.

3. The hand hygiene monitoring system according to claim 1, wherein the trajectory algorithm is defined as $$[s_{x_n}, s_{y_n}, s_{z_n}] = \left[ s_{x_{n-1}} + V_{x_{n-1}}\Delta t + \frac{1}{4}(a_{x_{n-1}}+a_{x_n})\Delta t^2, \right.$$
$$\left. s_{y_{n-1}} + V_{y_{n-1}}\Delta t + \frac{1}{4}(a_{y_{n-1}}+a_{y_n})\Delta t^2, s_{z_{n-1}} + V_{z_{n-1}}\Delta t + \frac{1}{4}(a_{z_{n-1}}+a_{z_{n-1}})\Delta t^2 \right];$$

wherein n is a signal scanning period, s(n) is a motion displacement function, [x,y,z] is a motion coordinate system, a(n) is the angular velocity, and V(n) is the instantaneous velocity, an initial position $s(t^0)=0$, $n>1$, and $\Delta t$ is a time interval value.

4. The hand hygiene monitoring system according to claim 3, wherein after detecting the trigger action, the processing chip is configured to change a current hand hygiene status into a state of clean-required; after detecting a hand washing action the processing chip is configured to change the current hand hygiene status into a clean state.

5. The hand hygiene monitoring system according to claim 4, further comprising: an alarm module, the alarm module is an acousto-optic, alarm device, and the acousto-optic, alarm device is connected to the processing chip and is used to prompt an examinee to judge a result.

6. A method of using the hand hygiene monitoring system according to claim 5, the method comprising following steps:

(1) identity recognition: activating the motion acquisition module to acquire a motion data of the person when the person enters a recognition area and is identified;

(2) hand washing detection: after entering a cleaning area, subjecting the person to hand washing detection by default; wherein the six-axis motion processing module of the motion acquisition module placed in the badge of the person acquires the movement direction data and trajectory data, the processing chip judges whether the movement of the person is a cleaning action, if the movement of the person is a cleaning action, changing a current state to a clean state; otherwise sending a message to the alarm module for warning;

(3) motion acquisition: after entering an operation area, during an operation of the person, acquiring the movement direction data and trajectory data of the person by the six-axis motion processing module placed in the badge of the person and sending to the processing chip until the person leaves the operation area;

(4) action judgment: using the movement direction data and trajectory data acquired in the step (3), the processing chip judges whether the current motion action of the person is the trigger action or not; if the motion action is the trigger action, the processing chip changes the current state as clean-required; otherwise sets the current state as clean; and (5) judgment after completion of the operation: after the person completes operation and enters the cleaning area, if the current state is the clean required, repeating the step (2); if the current state is the clean state, the person exits the cleaning area.

7. The method according to claim 6, wherein in the steps (2)-(5): from step (2) to step (5), the judgment process consists of a judgment interval period, and the judgement interval period is approximately 10 to 15 seconds.

* * * * *